(12) United States Patent
Sato

(10) Patent No.: US 7,627,364 B2
(45) Date of Patent: Dec. 1, 2009

(54) IMAGE APPARATUS AND METHOD, AND COMMUNICATION TERMINAL DEVICE

(75) Inventor: Hideo Sato, Tokyo (JP)

(73) Assignee: Sony Corporation, Tokyo (JP)

( * ) Notice: Subject to any disclaimer, the term of this patent is extended or adjusted under 35 U.S.C. 154(b) by 588 days.

(21) Appl. No.: 10/975,355

(22) Filed: Oct. 29, 2004

(65) Prior Publication Data

US 2005/0154318 A1 Jul. 14, 2005

(30) Foreign Application Priority Data

Oct. 30, 2003 (JP) ............................. 2003-371022
Apr. 30, 2004 (JP) ............................. 2004-135609

(51) Int. Cl.
*A61B 6/00* (2006.01)
(52) U.S. Cl. ..................... 600/473; 600/476; 340/5.83
(58) Field of Classification Search ................ 600/476, 600/310, 473; 382/115–116; 250/205, 214 AL; 356/39–42; 340/5.83
See application file for complete search history.

(56) References Cited

U.S. PATENT DOCUMENTS 6,353,753 B1 3/2002 Flock et al.
6,816,605 B2 * 11/2004 Rowe et al. .................. 382/115
6,889,075 B2 * 5/2005 Marchitto et al. ........... 600/473
7,239,909 B2 * 7/2007 Zeman ........................ 600/473
2002/0016533 A1 2/2002 Marchitto et al.
2002/0016536 A1 * 2/2002 Benni ......................... 600/323
2002/0035330 A1 3/2002 Cline et al.
2002/0183624 A1 * 12/2002 Rowe et al. .................. 600/476

FOREIGN PATENT DOCUMENTS

EP  1 335 329 A2  8/2003
WO  WO 03/014714 A1  2/2003

OTHER PUBLICATIONS

U.S. Appl. No. 10/546,038, filed Aug. 17, 2005, Sato.

* cited by examiner

*Primary Examiner*—Eric F Winakur
*Assistant Examiner*—Helene Bor
(74) *Attorney, Agent, or Firm*—Oblon, Spivak, McClelland, Maier & Neustadt, P.C.

(57) ABSTRACT

To realize downsizing. This invention provides an imaging apparatus with an irradiation means for irradiating a body with irradiation light stronger than light in the air coming to the body, a solid imaging element for performing photoelectric conversion on a pattern light of unique tissues obtained through the body, and a sensitivity adjustment means for adjusting the imaging sensitivity of the solid imaging element to the unique tissues by limiting the amount of a signal which is stored per unit time through the photoelectric conversion in the solid imaging element.

26 Claims, 17 Drawing Sheets

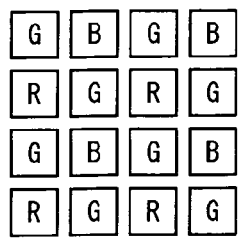
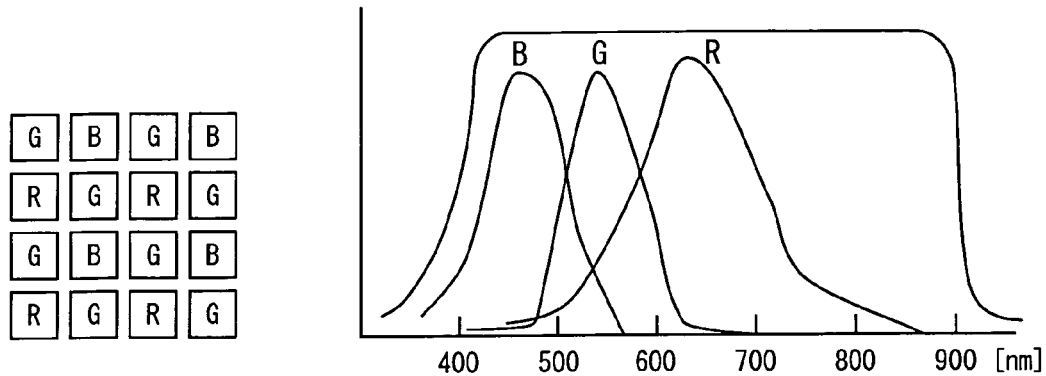
FIG. 3A  FIG. 3B
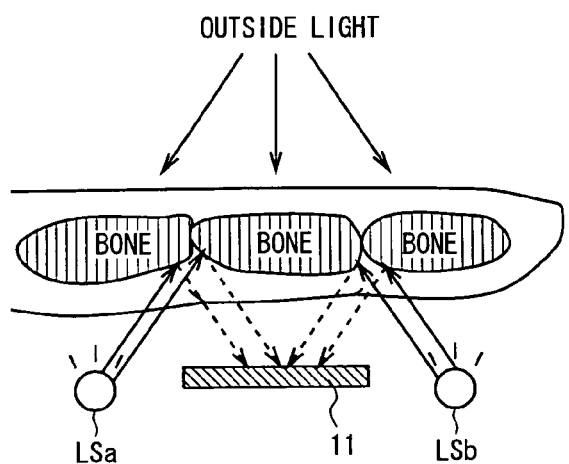
FIG. 4

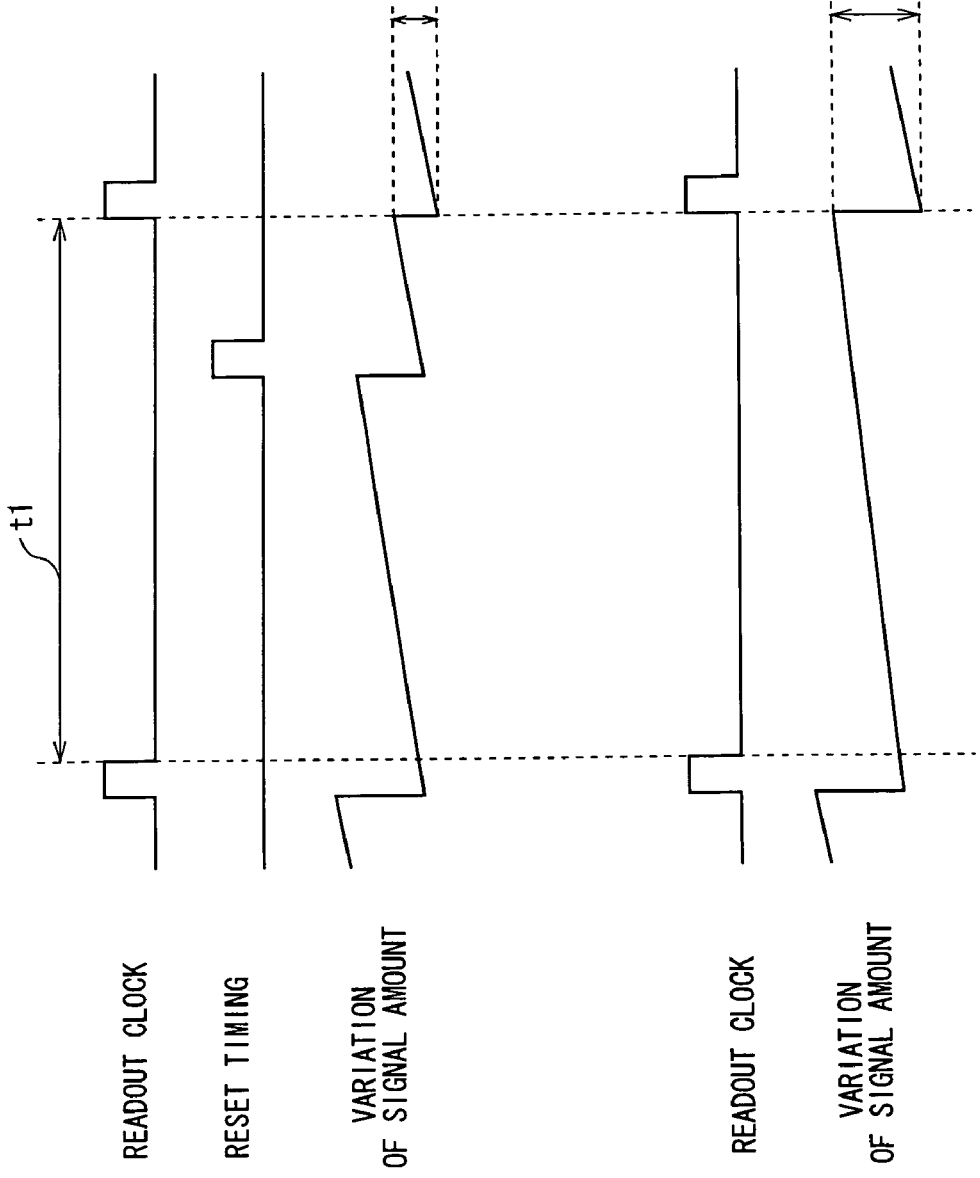

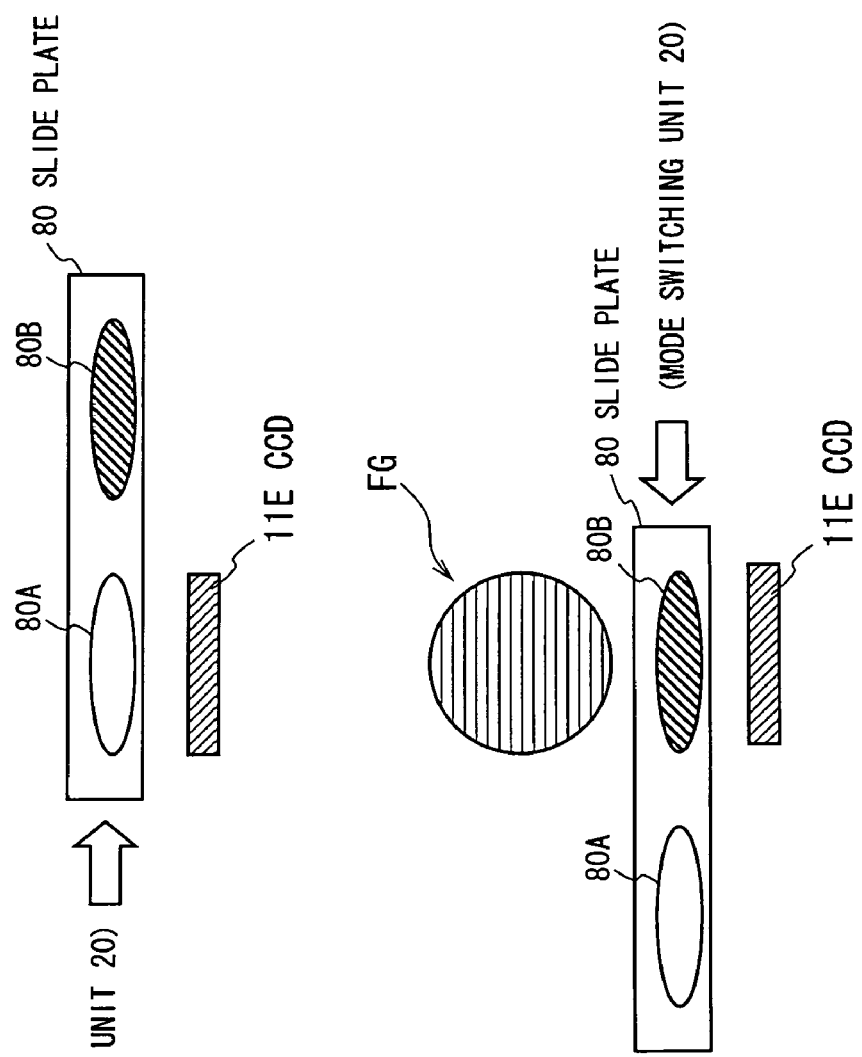

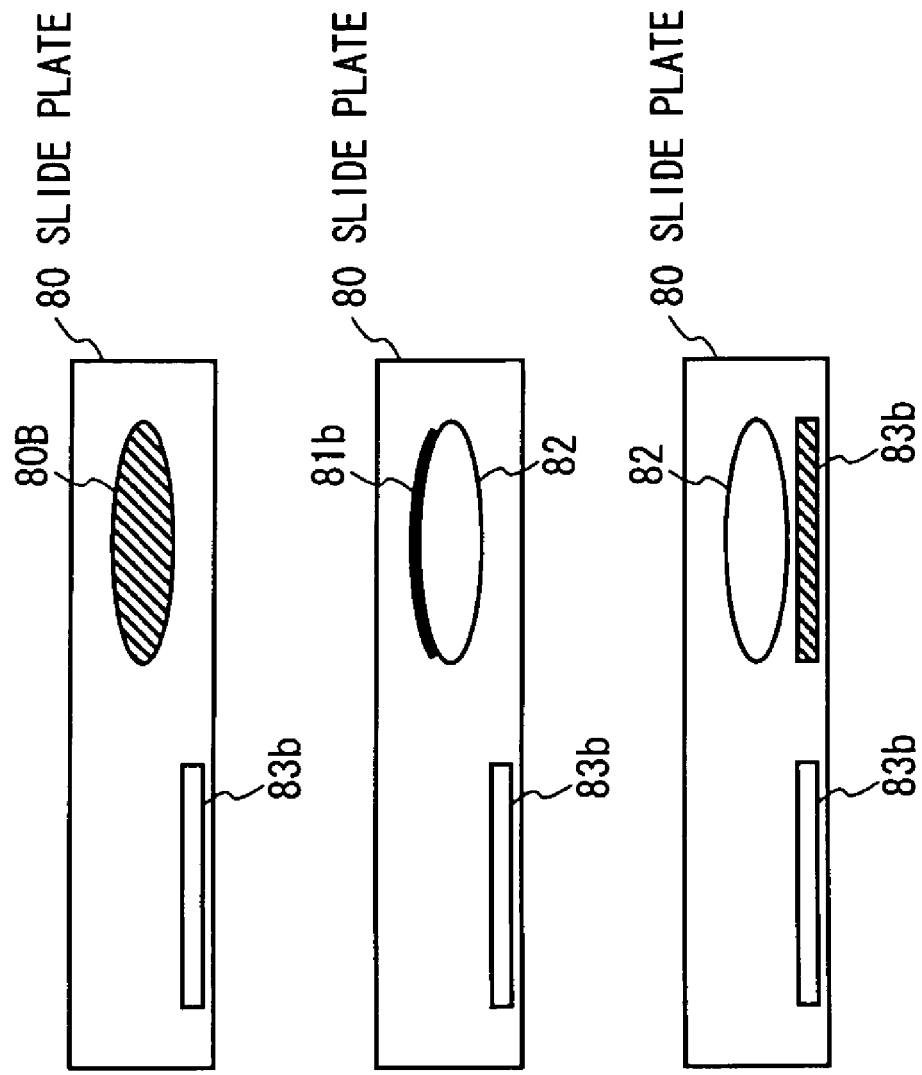

IMAGE APPARATUS AND METHOD, AND COMMUNICATION TERMINAL DEVICE

BACKGROUND OF THE INVENTION

1. Field of the Invention

This invention relates to an imaging apparatus and method, and a communication terminal device and, more particularly, is suitably applied to a case of creating information (hereinafter, referred to as identification information) certifying the validly of an identification target, for example.

2. Description of the Related Art

As identification information, unique body features such as iris, finger prints of fingers or a palm are used, which are difficult to be stolen by the third party.

Recently, a blood vessel formation pattern inside a body has been a focus of attention as one of such unique body features. Then an identification apparatus has been proposed to create the blood vessel formation pattern as identification information by using such a feature that deoxygenization hemoglobin (venous blood) or oxygenization hemoglobin (arterial blood) in blood vessels specifically absorb light (near-infrared light) of a near-infrared light band (for example, refer to Japanese Patent Laid-Open No. 2003-30632).

As an imaging apparatus used in an identification apparatus of this kind, an imaging apparatus 1 shown in FIG. 1 has been proposed.

This imaging apparatus 1 has a laser light source 2 which emits near-infrared light. On a light path of the near-infrared light emitted from the laser light source 2, a first filter 3 for letting light of specified near-infrared light band out of the near-infrared light get through, a second filter 4 for letting light of a near-infrared light band which is absorbed in hemoglobin in blood vessels, out of the light which passed through the first filter 3, and an imaging element 5 are arranged in order.

In this case, in a situation where, for example, a human finger FG is inserted between the first filter 3 and the second filter 4, the imaging apparatus 1 emits near-infrared light from the light source 2 to irradiate the finger FG with this via the first filter 3. Since this near-infrared light is specifically absorbed in the intrinsic hemoglobin inside the blood vessel tissues in the finger FG, near-infrared light which passed through the finger FG is entered in the imaging element 5 through the second filter 4 as blood vessel pattern light representing the formation pattern of the blood vessel tissues.

Then the imaging element 5 performs photoelectric conversion on the blood vessel pattern light with a plurality of photoelectric conversion elements which is arranged in a reticular pattern in correspondence with pixels, to create a blood vessel image signal, and sends this to an information creation unit 6. The information creation unit 6 creates identification information based on the blood vessel image signal and outputs this to the outside.

In addition, this imaging apparatus 1 is provided with a shielding unit 7 for shielding light (outside light) in the air coming to the finger FG, thereby eliminating influences of the outside light on the near-infrared light emitted from the light source 2. Therefore, the imaging apparatus 1 is capable of creating a blood vessel image signal in which the blood vessel tissues inside the finger FG are faithfully reflected.

By the way, such the imaging apparatus 1 has a large-scale problem because, to create a blood vessel image signal in which blood vessel tissues are faithfully reflected, the physical shielding unit 7 should be provided to eliminate influences of the outside light on near-infrared light emitted from the light source 2, the physical shielding unit 7 covering not only all units 2 to 5 on the light path of the near-infrared light emitted from the light source 2 but also the finger FG.

In addition, to install the blood vessel imaging function of the imaging apparatus 1 in a communication terminal device such as a portable telephone or a Personal Digital Assistant (PDA) to determine based on identification information which is obtained from the imaging apparatus 1 in communicating with the outside, whether the communication terminal device is being used by the third party, the communication terminal device is hard to be put into practical use due to the shielding unit 7.

SUMMARY OF THE INVENTION

This invention has been made in view of foregoing, and intends to propose an imaging apparatus which can be downsized and its method, and a communication terminal device capable of offering substantially simple use.

The foregoing objects and other objects of the invention have been achieved by the provision of an imaging apparatus comprising: an irradiation means for irradiating a body with irradiation light stronger than light in the air coming to the body; a solid imaging element for performing photoelectric conversion on a pattern light of unique tissues obtained through the body; and a sensitivity adjustment means for adjusting the imaging sensitivity of the solid imaging element to the unique tissues by limiting the amount of a signal which is stored per unit time through the photoelectric conversion in the solid imaging element.

Further, this invention provides an imaging method with: a first step of irradiating a body with irradiation light stronger than light in the air coming to the body; a second step of performing photoelectric conversion on a pattern light of unique tissues obtained through the body; and a third step of adjusting the imaging sensitivity of a solid imaging element to the unique tissues by limiting the amount of a signal which is stored per unit time through the photoelectric conversion in the solid imaging element.

Furthermore, this invention provides a communication terminal device having a communication function with: an irradiation means for irradiating a body with irradiation light stronger than light in the air coming to the body; a solid imaging element for performing photoelectric conversion on a pattern light of unique tissues obtained through the body; a sensitivity adjustment means for adjusting the imaging sensitivity of the solid imaging element to the unique tissues by limiting the amount of a signal which is stored per unit time through the photoelectric conversion in the solid imaging element; and an information registration means for registering a pattern signal obtained as the imaging result of the solid imaging element in an information storage means as a determination index which is used to determine whether transmission of information is allowed.

According to this invention, with the imaging apparatus and its method, the amount of the signal which is stored in the solid imaging element as the result of the photoelectric conversion of the pattern light and the outside right arriving at this time can be relatively reduced. Therefore, imaging can be performed without physically shielding the light path of the irradiation light and the imaging target and without substantial influences of the outside light on the imaging sensitivity of the solid imaging element to the pattern light. As a result, downsizing can be realized.

In addition, according to this invention, with the communication terminal device, imaging can be performed without physically shielding the light path of the irradiation light and the imaging target and without substantial influences of the outside light on the imaging sensitivity of the solid imaging element to the pattern light. As a result, it can be easily determined based on the pattern signal registered in the information storage means whether an abuser is using the device, thus making it possible to improve substantial use easily.

The nature, principle and utility of the invention will become more apparent from the following detailed description when read in conjunction with the accompanying drawings in which like parts are designated by like reference numerals or characters.

BRIEF DESCRIPTION OF THE DRAWINGS

In the accompanying drawings:

FIGS. 3A and 3B are schematic diagrams showing the construction and characteristics of an ultraviolet cut filter;

FIG. 4 is a schematic diagram showing the arrangement of near-infrared light sources and a light flow of near-infrared light;

FIGS. 5A and 5B are schematic diagrams explaining an electronic shutter;

FIGS. 12A and 12B are schematic diagrams explaining how to select incident light;

FIG. 13A and 13B and 14A to 14C are schematic diagrams showing construction variations of a slide plate;

DETAILED DESCRIPTION OF THE EMBODIMENT

Preferred embodiments of this invention will be described with reference to the accompanying drawings:

(1) First Embodiment (1-1) Construction of Imaging Apparatus

Figure 2:
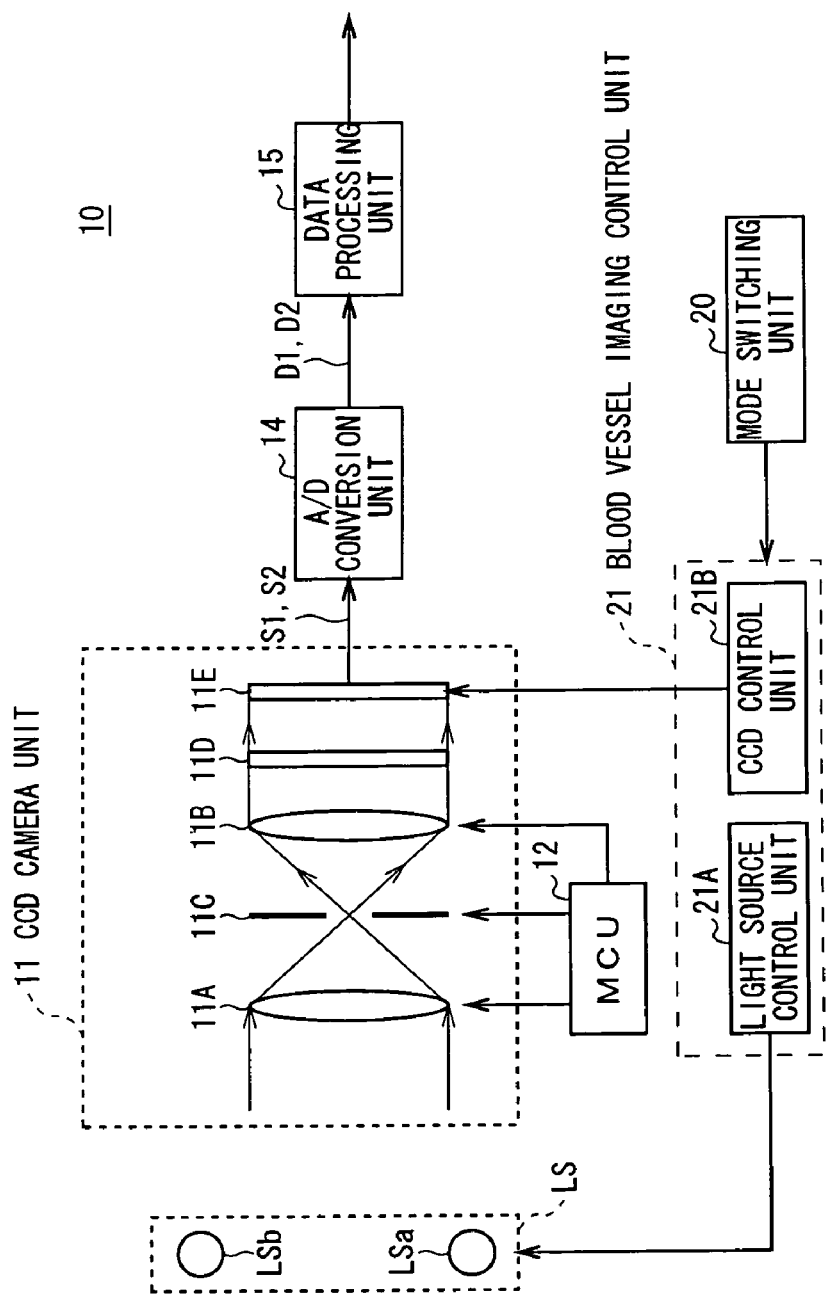
FIG. 2 is a schematic diagram showing the construction of an imaging apparatus according to the first embodiment.

FIG. 2 shows an imaging apparatus 10 according to this embodiment. This imaging apparatus 10 executes a mode (hereinafter, referred to as normal imaging mode) to take pictures of subjects such as bodies and backgrounds as imaging targets.

In this case, a CCD camera unit 11 guides outside light in the air coming from a front subject, to a CCD 11E via a lens 11A, an aperture 11C, a lens 11B, and an ultraviolet cut filter 11D in order.

At this time, a Micro Control Unit (MCU) 12 adjusts the amount of the outside light entered into the CCD 11E by controlling the aperture 11C with an automatic exposure control process and also adjusts a focus distance and focus position by controlling the positions of the lens 11A and 11B with an auto focus control process.

This ultraviolet cut filter 11D comprises an RGB filter which has a pixel arrangement as shown in FIG. 3A and lets visible light and near-infrared light get through as shown in FIG. 3B.

The CCD 11E performs photoelectric conversion on outside light entered via the ultraviolet cut filter 11D, with a plurality of photoelectric conversion elements arranged in correspondence with the pixels, and reads a charge signal stored through the photoelectric conversion in each photoelectric conversion element, as an image signal Si according to prescribed readout clock, and sends this to an Analog/Digital (A/D) conversion unit 14.

The A/D conversion unit 14 converts the image signal S1 to a digital image signal D1 and sends this to a data processing unit 15.

The data processing unit 15 stores the digital image signal D1 in an internal memory (not shown), for example.

As described above, the imaging apparatus 10 executes the normal imaging mode and can take pictures of subjects such as bodies and backgrounds as imaging targets.

In addition to the above units, near-infrared light sources LS (LSa and LSb) for irradiating the arrival direction side of the outside light with near-infrared light are arranged on the same plane as the arrangement position of the CCD camera unit 11 as shown in FIG. 4, to execute a mode (hereinafter, referred to as blood vessel imaging mode) to image the blood vessel tissues inside a finger FG positioned in the irradiation direction, as an imaging target.

In this case, when prescribed operation to image blood vessels is performed with an operating unit (not shown), a mode switching unit 20 (FIG. 2) operates both a light source control unit 21A and a CCD control unit of a blood vessel imaging control unit 21.

The light source control unit 21A controls the near-infrared light sources LS so as to irradiate the finger FG with near-infrared light stronger than the outside light which is normally obtained in the air.

As shown in FIG. 4, this near-infrared light is specifically absorbed in the intrinsic hemoglobin of the blood vessel tissues (not shown) in the finger FG, and passes through or is reflected by the other tissues. The outside light coming at this time, on the other hand, is attenuated by being blocked by bones or the like and can be ignored because of the hearinfrared light stronger than the outside light. Therefore, the near-infrared light obtained through the finger FG is guided to the CCD 11E via the lens 11A, the aperture 11C, the lens 11B and the ultraviolet cut filter 11D, shown in FIG. 2, in order, as blood vessel pattern light representing the formation pattern of the blood vessel tissues.

Then each photoelectric conversion element of the CCD 11E stores a charge signal obtained as a result of the photoelectric conversion of the entered blood vessel pattern light.

At this time, the CCD control unit 21B adjusts the imaging sensitivity of the CCD 11E to the blood vessel pattern light by electrically limiting the amount of the charge signal stored in each photoelectric conversion element of the CCD 11E with an exposure time control process called an electronic shutter.

Specifically, as shown in FIGS. 5A and 5B, the CCD control unit 21B resets the amount of a charge signal being stored in each photoelectric conversion element of the CCD 11E, at prescribed reset timing in a period (hereinafter, referred to as charge storage period) t1 from falling of a readout clock till rising of a next readout clock (FIG. 5A), to limit it to the amount of a charge signal (FIG. 5A) fewer than the amount of a charge signal (FIG. 5B) read according to the readout clock in the normal imaging mode.

Figure 6A:
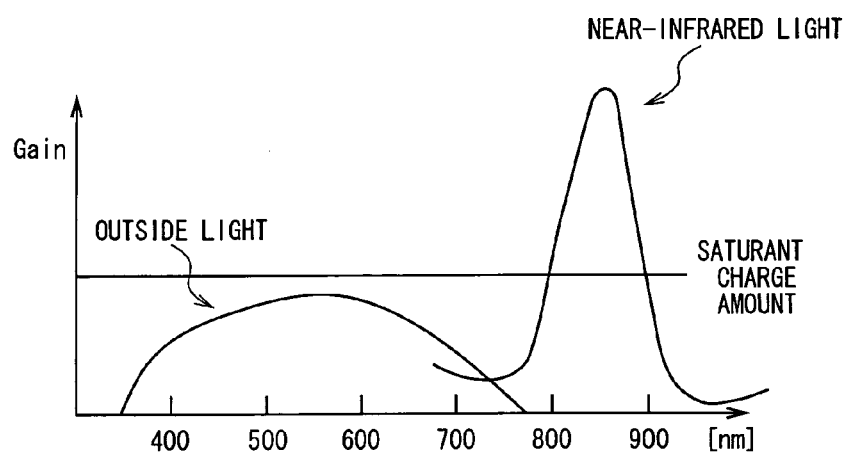
FIGS. 6A and 6B are schematic diagrams explaining adjustment of imaging sensitivity by the electronic shutter.
Figure 6B:
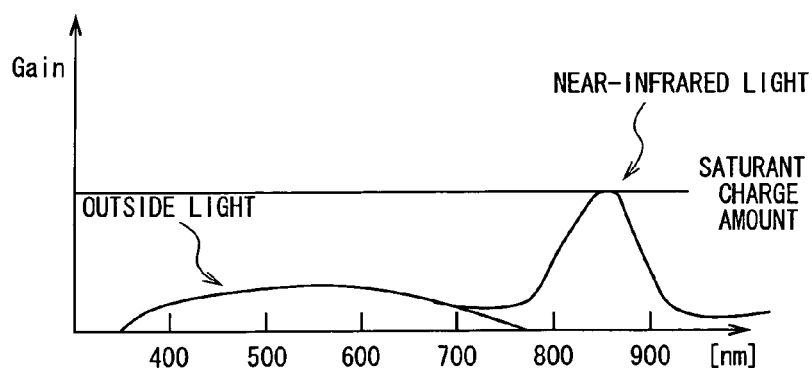

As a result, as shown in FIG. 6A, each photoelectric conversion element of the CCD 11E can previously prevent a charge signal being stored in the photoelectric conversion element from being saturated during the charge storage period t1 due to the stronger near-infrared light emitted from the near-infrared light sources LS than the outside light. In addition, as shown in FIG. 6B, the amount of the charge signal being stored in each photoelectric conversion element as a result of the photoelectric conversion of the blood vessel pattern light and the outside light coming at this time is relatively reduced, with the result that the imaging sensitivity of the CCD 11E to the blood vessel pattern light is not substantially influenced by the outside light.

Therefore, in the CCD 11E, the charge signal limited with the exposure time control process of the CCD control unit 21B is read as a blood vessel image signal S2 (FIG. 2) in which the blood vessels inside the finger FG are faithfully reflected, at the readout timing of a readout clock supplied from the clock generator 13, and is converted into a digital blood vessel image signal D2 via the A/D conversion unit 14.

The data processing unit 15 binarizes the digital blood vessel image signal D2 supplied via the A/D conversion unit 14, extracts a combination of the forks of the blood vessels out of the resultant binarized blood vessel image as a blood vessel formation pattern, and stores this in the internal memory (not shown). Therefore, the data processing unit 15 can prevent a direct theft from the body, as compared with a case of extracting fingerprints or the like on a body surface, so that this formation pattern can be stored in the internal memory (not shown) as highly confidential information.

As described above, the imaging apparatus 10 executes the blood vessel imaging mode and is capable of imaging the blood vessel tissues inside a human finger FG.

In addition to the above configuration, the light source control unit 21A is designed to irradiate the finger FG with light including both light of a wavelength which is specifically absorbed in oxygenation hemoglobin and light of a wavelength which is specifically absorbed in deoxygenization hemoglobin out of the hemoglobin (transport protein) of the blood vessel tissues inside the finger FG, i.e., near-infrared light of a wavelength of a range from 700 to 900 nm.

Therefore, the image apparatus 10 is capable of creating with the CCD camera unit 11, the blood vessel image signal S2 in which the capillary tissues containing oxygenation and deoxygenization hemoglobin are faithfully reflected, and as a result, more highly confidential information can be obtained with security.

Figure 1:
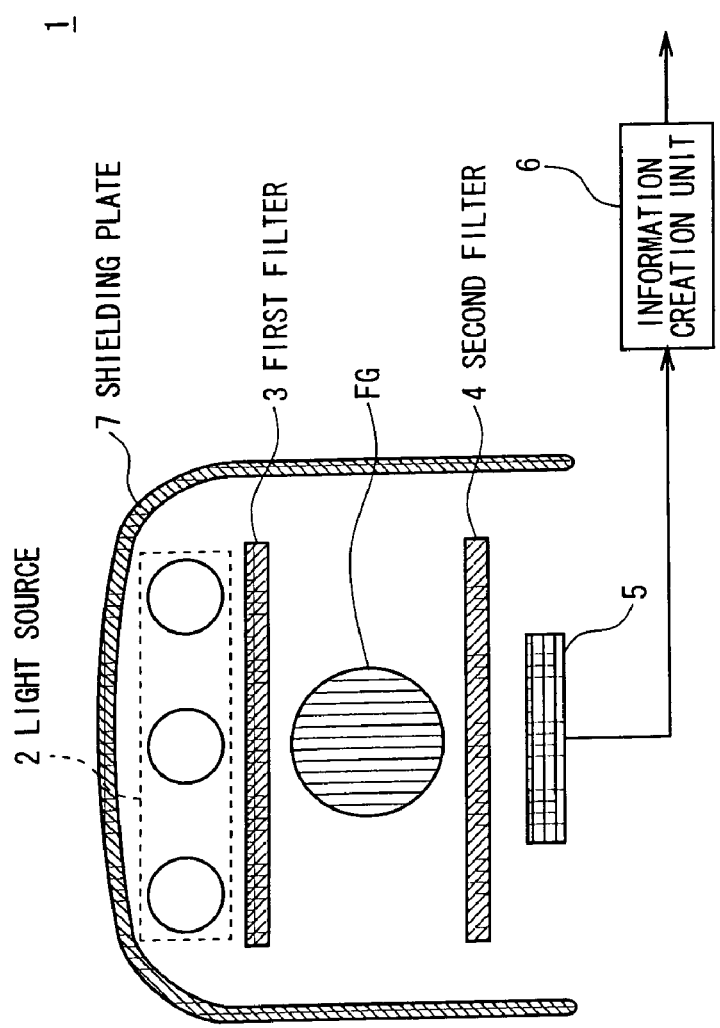
FIG. 1 is a schematic diagram showing a conventional imaging apparatus.

In addition, in this case, the imaging apparatus 10 can previously prevent a case where hemoglobin is changed due to concentration of energy to the blood vessel tissues, as compared with a case of irradiating a finger FG with near-infrared light of only a wavelength which is specifically absorbed in the oxygenation and deoxygenization hemoglobin. In addition, unlike the imaging apparatus 1 shown in FIG. 1, a simple design can be realized without providing the laser light source 2 and the bandwidth limitation filters 3 and 4 for limiting a bandwidth to emit light which is specific for blood vessel tissues, and an S/N ratio can be improved.

(1-2) Operation and Effects of First Embodiment

According to the above configuration, this imaging apparatus 10 irradiates a finger FG with near-infrared light stronger than the outside light which is normally obtained in the air, from the near-infrared light sources LS, and performs the photoelectric conversion on the blood vessel pattern light obtained through the finger FG, with the photoelectric conversion elements of the CCD 11E.

Then the imaging apparatus 10 adjusts the imaging sensitivity of the CCD 11E to the blood vessel tissues by limiting the amount of a charge signal per the charge storage period t1, which is stored through the photoelectric conversion in each photoelectric conversion element of the CCD 11E.

Therefore, this imaging apparatus 10 can relatively reduce the amount of the charge signal being stored in each photoelectric conversion element as a result of the photoelectric conversion of the blood vessel pattern light and the outside light coming at this time, and thus can perform imaging without physically shielding the light path of the near-infrared light and the imaging target and without substantial influences of the outside light on the imaging sensitivity of the CCD 11E to the blood vessel pattern light. As a result, downsizing can be realized.

In addition, in this case, in the imaging apparatus 10, the near-infrared light sources LS (LSa and LSb) for irradiating the arrival direction side of the outside light with near-infrared light are arranged on the same plane as the arrangement position of the CCD camera unit 11, so as to irradiate the opposite side of the outside light entering to the CCD 11E of the CCD camera unit 11 with the near-infrared light.

Therefore, only by putting the finger FG in front of the CCD camera unit 11, this imaging apparatus 10 can perform imaging without substantial influences of the outside light because the coming outside light is attenuated by the bones or the like of the finger FG.

Further, in this case, the imaging apparatus 10 operates the light source control unit 21A and the CCD control unit 21 with the mode switching unit 20 in the blood vessel imaging mode out of the normal imaging mode and the blood vessel imaging mode.

Therefore, this imaging apparatus 10 can reduce power consumed in the light source control unit 21A and can be downsized because the CCD camera unit 11 can be used for both the imaging of normal subjects and imaging of blood vessels.

According to the above configuration, a finger FG is irradiated with near-infrared light stronger than the outside light which is normally obtained in the air, from the near-infrared light sources LS, and the imaging sensitivity of the CCD 11E to the blood vessel tissues is adjusted by limiting the amount of a charge signal per the charge storage period t1 which is stored in each photoelectric conversion element of the CCD 11E as a result of the photoelectric conversion of the blood vessel pattern light obtained through the finger FG. Therefore, the imaging can be performed without physically shielding the light path of the near-infrared light and the imaging target and without substantial influences of the outside light on the imaging sensitivity of the CCD 11E to the blood vessel pattern light. Thus significant downsizing can be realized.

(2) Second Embodiment (2-1) External Construction of Portable Telephone

Figure 7:
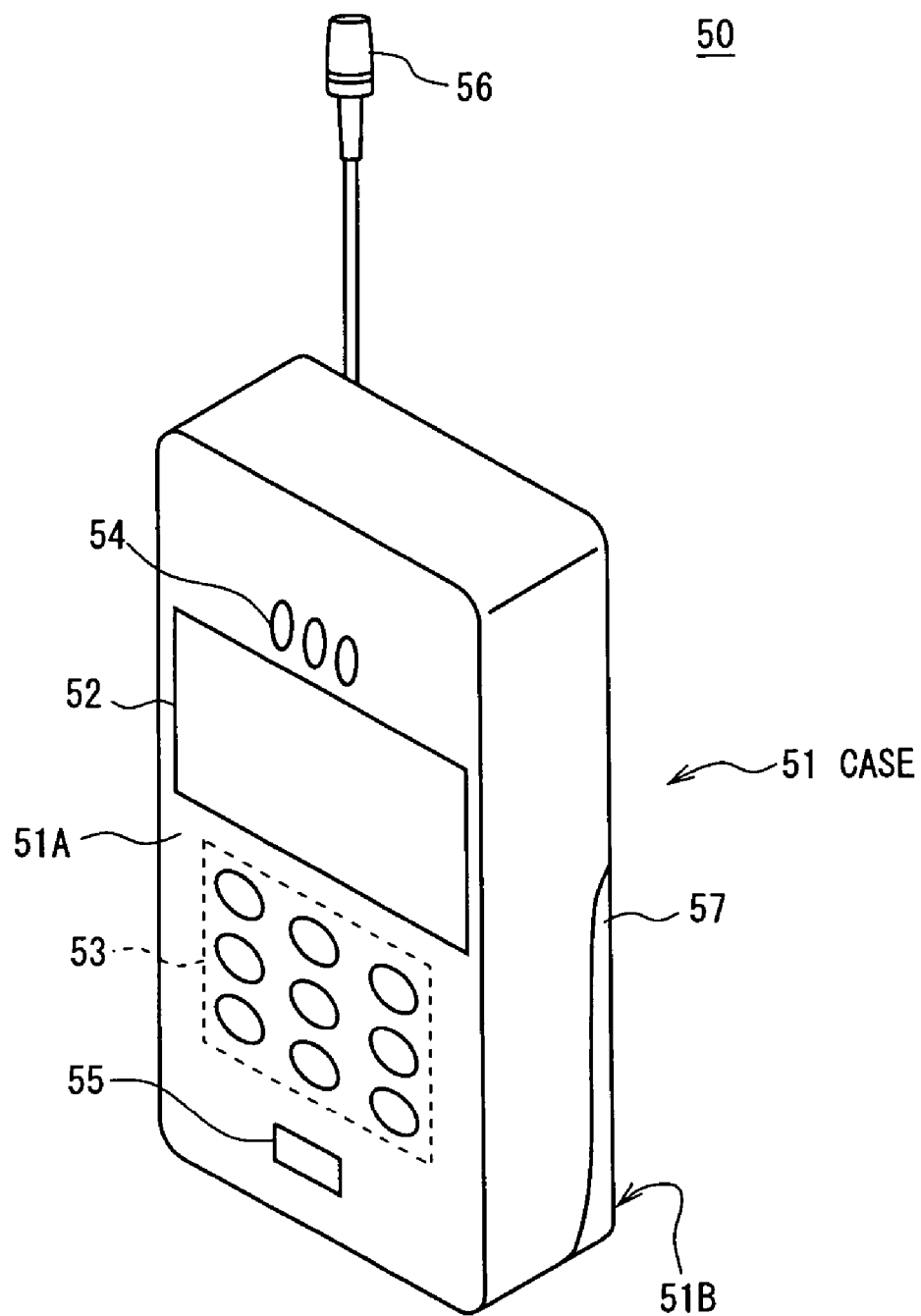
FIG. 7 is a schematic diagram showing the external construction of a portable telephone according to the second embodiment.

FIG. 7 shows an external construction of a portable telephone 50. Referring to this figure, this portable telephone 50 has a thin rectangular solid case 51, and is provided with a display unit 52, an operating part 53 composed of a plurality of operating buttons, a loudspeaker 54, and a microphone 51B on its front side 51A. On the back side 51B, on the other hand, a telescopic antenna 56 and a removable power battery 57 are provided.

Figure 8B:
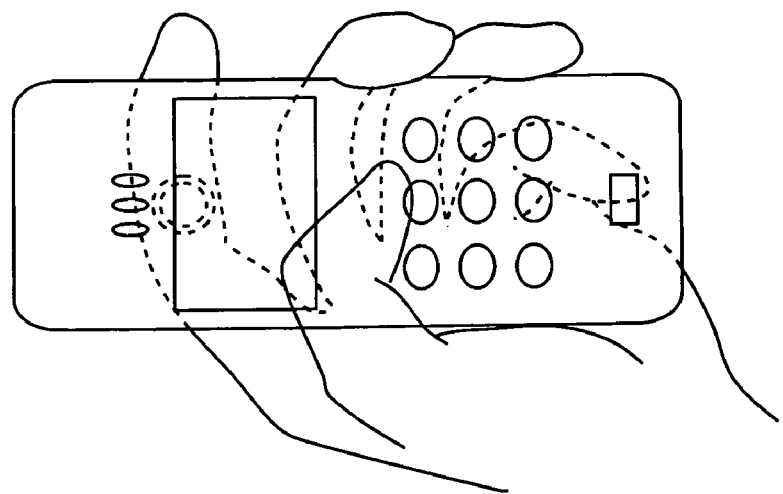
FIGS. 8A and 8B are schematic diagrams showing how to perform imaging.
Figure 8A:
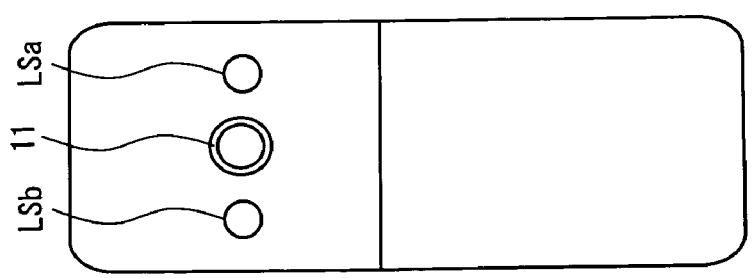

Further, referring to FIG. 8A, this portable telephone 50 is provided with a CCD camera unit 11, for example, on the back side 51B to take pictures of normal subjects such as people and scenery.

In addition to the above units, in this portable telephone 50, near-infrared light sources LS (LSa and LSb) for irradiating the arrival direction side of outside light with near-infrared light are arranged on the same plane as the arrangement position of the CCD camera unit 11. Similarly to a case shown in FIG. 4, the near-infrared light sources LS (LSa, LSb) irradiate a finger existing on the CCD camera unit 11 with near-infrared light to take a picture of the finger, so as to use the imaging result as information for personal identification.

In this case, in this portable telephone 50, as shown in FIG. 8B, the CCD camera unit 11 is arranged at such a position that a prescribed finger of a user holding the portable telephone 50 can be positioned on the CCD camera unit 11. That is, the personal identification can be performed while the user is holding the portable telephone 50.

(2-2) Internal Construction of Portable Telephone

Figure 9:
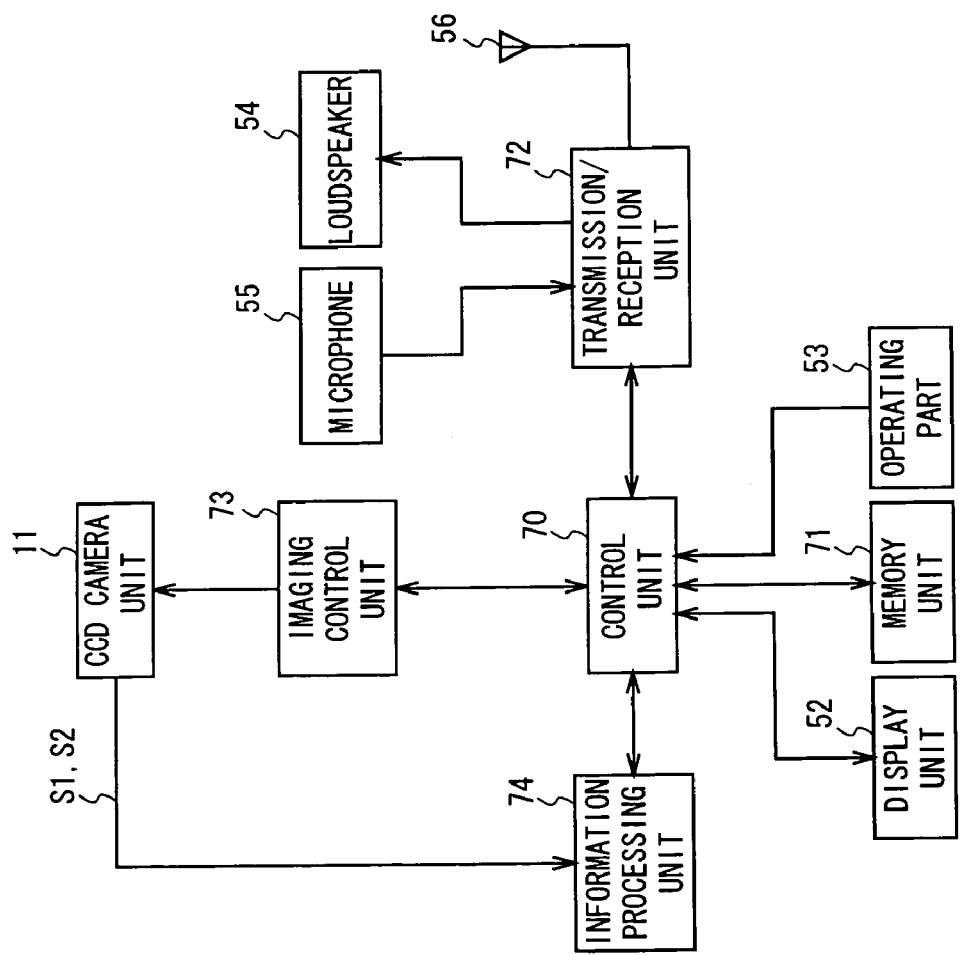
FIG. 9 is a block diagram showing the circuit construction of the portable telephone.

FIG. 9 shows an internal construction of the portable telephone 50. This portable telephone 50 is composed of the display unit 52, the operating part 53, a memory unit 71, a transmission/reception unit 72, an imaging control unit 73 and an information processing unit 74, which are connected to a control unit 70. In addition, to the transmission/reception unit 72, the loudspeaker 54, the microphone 55, and the antenna 56 are connected. The CCD camera unit 11 (FIG. 2) having the same construction as the first embodiment is connected to the imaging control unit 73.

In addition, the imaging control unit 73 is composed of the MCU 21 and the blood vessel control unit 21 shown in FIG. 2. The information processing unit 74 is composed of the A/D converter 14 and the data processing unit 15 shown in FIG. 2. The memory unit 71 stores various programs and various information including personal information.

This control unit 70 reads a program from the memory unit 71 and puts it in an internal work memory so as to entirely control the portable telephone 50 according to the program and to mediate processing results of each unit based on the control or execute various processes by itself.

The transmission/reception unit 72 modulates and then amplifies various signals entered from the microphone 55 and the control unit 70, and sends the resultant up-link wave signal to a base station (not shown) via the antenna 56. In addition, the transmission/reception unit 72 receives a down-link wave signal from a base station (not shown) via the antenna 56, amplifies and then demodulates the signal, and sends the resultant signal to the loudspeaker 54 or the control unit 70.

By the way, when the control unit 70 receives a normal imaging command from the operating part 53, it gives this command to the imaging control unit 73.

In this case, the imaging control unit 73 executes the normal imaging processing mode described with reference to FIG. 2 to control the optical system of the CCD camera unit 11 with the automatic exposure control process and the auto focus control process. In this state, the CCD camera unit 11 performs the photoelectric conversion on the outside light in the air coming from the front subject to create an image signal S1, and stores this in the memory unit 71 as a digital image signal via the information processing unit 74 and the control unit 70 in order.

On the other hand, when the control unit 70 receives a blood vessel registration command from the operating unit 53 in a situation where a prescribed finger holding the portable telephone 50 is placed on the CCD camera unit 11, it gives this command to the imaging control unit 73.

In this case, the imaging control unit 73 executes the blood vessel imaging mode described with reference to FIG. 2, to irradiate the finger with near-infrared light stronger than the outside light from the near-infrared light sources LS (FIG. 8A) and adjust the imaging sensitivity of the CCD 11E of the CCD camera unit 11 (FIG. 2) to the blood vessel pattern light with the exposure time control process (electronic shutter).

In this state, the CCD camera unit 11 performs the photoelectric conversion on the blood vessel pattern light obtained through the finger by irradiating the finger from the near-infrared light sources LS, to create and send a blood vessel image signal S2 to the information processing unit 74. The information processing unit 74 extracts the blood vessel formation pattern of the prescribed part from the blood vessel image of the digital blood vessel image signal which is a result of the A/D conversion of the blood vessel image signal S2, and registers the extracted unique blood vessel formation pattern in the memory unit 71 as identification information.

On the other hand, when the control unit 70 receives a transmission command to transmit a digital image signal S1 as personal information being stored in the memory unit 71, from the operating part 53, it notifies a user operating the operating part 53 via the display unit 52 that blood vessels should be imaged.

Then when the control unit 70 receives, as a response to the notification, a blood vessel imaging command from the operating part 53 in a situation where the prescribed finger holding the portable telephone 50 is positioned on the CCD camera unit 11 (FIG. 8B), it gives this command to the imaging control unit 73. In this case, the imaging control unit 73 executes the blood vessel imaging mode as well. The information processing unit 74 sends the blood vessel formation pattern of the forefinger of the user, which is extracted based on the blood vessel image signal S2 given from the CCD camera unit 11 to the control unit 70 as matching target information, as in the case of registering blood vessels.

Figure 10:
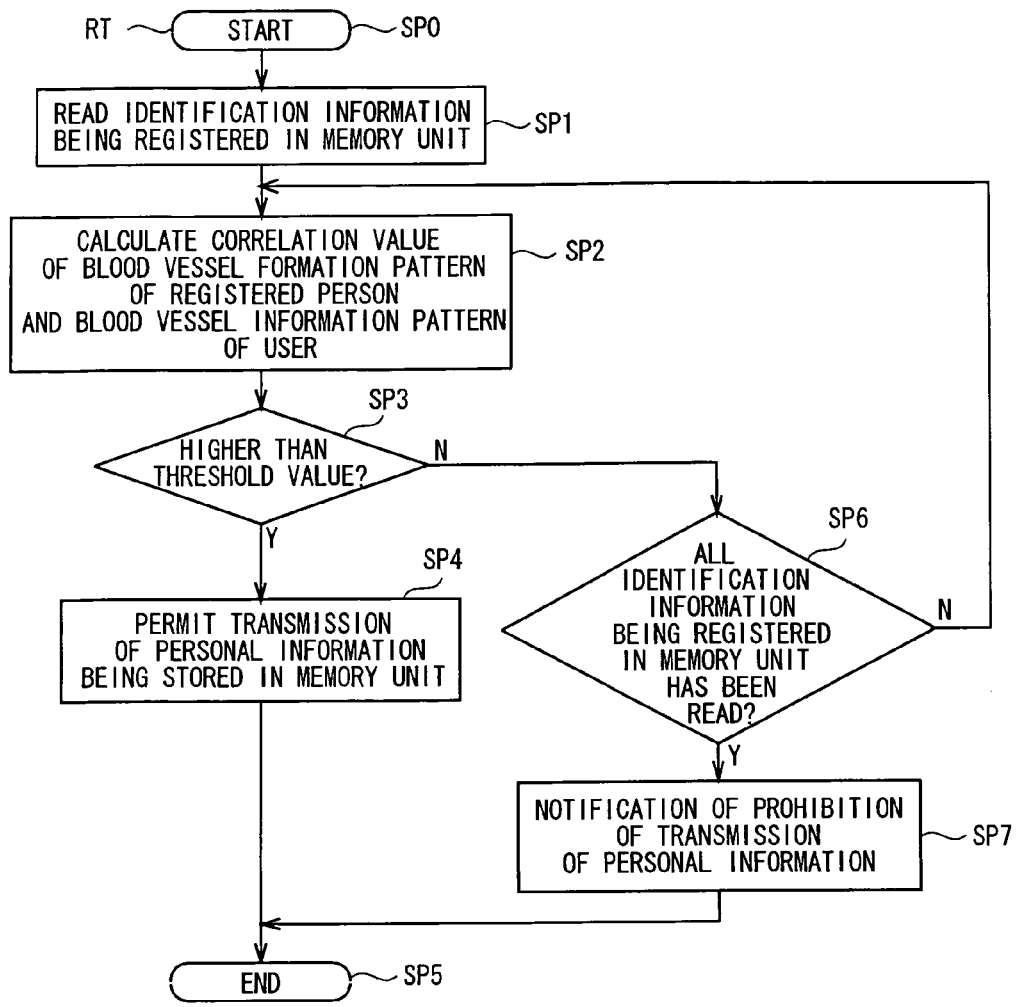
FIG. 10 is a flowchart showing an identification procedure.

When the control unit 70 receives the matching target information from the information processing unit 74, it executes an identification process with an identification procedure shown in FIG. 10.

That is, the control unit 70 starts this identification procedure RT from step SP0, and at step SP1, reads identification information being registered in the memory unit 71. At step SP2, the control unit 70 compares the blood vessel formation pattern of this identification information with the blood vessel formation pattern of the matching target information received from the information processing unit 74, to calculate a correlation value of the blood vessel formation patterns. At step SP3, the control unit 70 determines whether this correlation value is higher than a preset threshold value.

When an affirmative result is obtained here, this means that the user of the portable telephone 50 is a previously registered person, that is, a rightful user. At this time, the control unit 70 permits the transmission of the personal information being stored in the memory unit 71 at step SP4, and then at step 5, finishes this identification procedure RT.

When a negative result is obtained, on the contrary, this means that the user of the portable telephone 50 may not be a previously registered person, that is, may be an illegal user. At this time, at step SP6, the control unit 70 determines whether all the identification information being registered in the memory unit 71 are compared.

When not all the identification information is compared, the control unit 70 returns back to step SP1 to repeat the above process. When the control unit 70 has finished the comparison process for all the identification information, this means that the user of the portable telephone 50 has not been registered. At this time, at next step SP7, the control unit 70 notifies the user via the display unit 52 that the transmission of the personal information is not allowed, and then at step SP5 finishes this identification procedure RT.

As described above, when personal information being stored in the memory unit 71 is transmitted outside the portable telephone 50, the control unit 70 determines whether the user of the portable telephone 50 is a rightful user. And only when the user is a rightful user, the transmission of the personal information is allowed.

(2-3) Operation and Effects of Second Embodiment

According to the above configuration, this portable telephone 50 is provided with the imaging control unit 73 and the information processing unit 74. With these units, as in the above-described case of the first embodiment, a finger FG is irradiated with near-infrared light stronger than the outside light which is normally obtained in the air from the near-infrared light sources LS, and the imaging sensitivity of the CCD 11E to blood vessel tissues is adjusted by limiting the amount of a charge signal per the charge storage period t1 (FIGS. 5A and 5B) which is stored in each photoelectric conversion element as a result of the photoelectric conversion of the blood vessel pattern light obtained through the finger FG with each photoelectric conversion element of the CCD 11E.

Then the portable telephone 50 registers the blood vessel image signal S2 obtained as a result of the process of the blood vessel imaging function (imaging control unit 73 and information processing unit 74), in the memory unit 71 as a determination index (identification information (blood vessel formation pattern)) which is used for determining whether the transmission of personal information is allowed.

Therefore, this portable telephone 50 can perform imaging without physically shielding the light path of the near-infrared light and the imaging subject and without substantial influences of the outside light on the imaging sensitivity of the CCD 11E to the blood vessel pattern light. Therefore, it can be determined by using the blood vessel formation pattern being registered in the memory unit 71 as an imaging result, whether a user who wants to send personal information is an illegal user, without loosing various functions such as the portability and communication property of the portable telephone 50 due to a physical shielding entity.

According to the above configuration, the blood vessel imaging function is installed, and a blood vessel image signal S2 obtained as a result of the process of the blood vessel imaging function is registered in the memory unit 71 as a determination index for determining whether the transmission of personal information is allowed. Therefore, it can be easily determined by using the blood vessel formation pattern being registered in the memory unit 71 as an imaging result whether an illegal user is using the portable telephone, without loosing various properties including the portability and communication property of the portable telephone 50 due to a physical shielding entity, thus making it possible to easily improve substantial use.

(3) Other Embodiments

Note that the above embodiments described a case where the outputs of the near-infrared light sources LS are controlled so as to emit near-infrared light stronger than the outside light, as an irradiation means for irradiating a body with irradiation light stronger than the light in the air coming to the body. This invention, however, is not limited to this and the strength of the light in the air is detected and the outputs of the near-infrared light sources LS can be controlled according to the detection result. By doing so, near-infrared light of a strength suitable for a blood vessel imaging place can be emitted, resulting in reducing power consumption as compared with a case of always emitting near-infrared light of the same strength.

Further, in this case, as the irradiation light, light including light of a wavelength which has a specificity for the blood vessel tissues of both arterial blood and venous blood in a body is emitted. This invention, however, is not limited to this and light including light of a wavelength which has a specificity for the blood vessel tissues of one of the arterial blood and the venous blood can be emitted, or light including light of a wavelength which has a specificity for specific tissues other than the blood vessel tissues inside the body can be emitted.

Furthermore, in this case, a finger of a body is applied as an irradiation target. This invention, however, is not limited to this and another part such as an aperture and the whole body can be applied.

Further, the above embodiments have described a case where the near-infrared light sources LS (LSa, LSb) arranged on the same plane as the arrangement position of the CCD camera unit 11 irradiate the arrival direction side of the outside light with near-infrared light as an irradiation means for irradiating a body with irradiation light stronger than light in the air coming to the body. This invention, however, is not limited to this and an irradiation target can be irradiated with the near-infrared light from various directions.

Figure 11A:
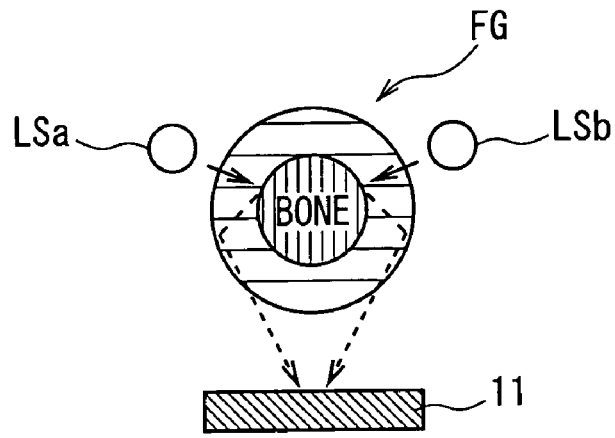
FIGS. 11A to 11C are schematic diagrams showing the arrangement of light sources.
Figure 11B:
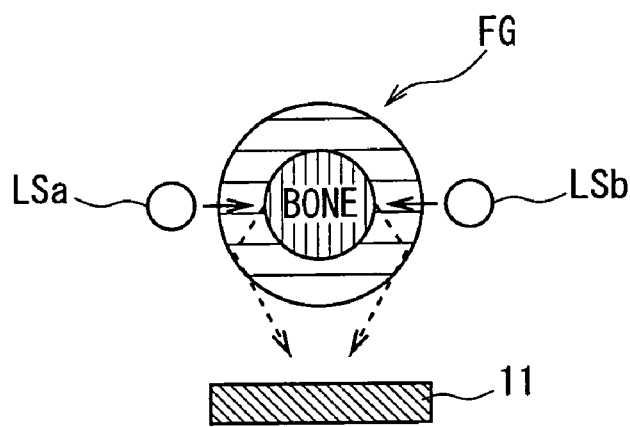
Figure 11C:
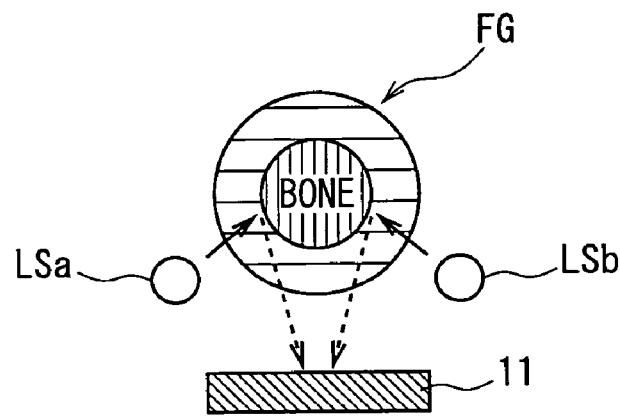

For example, near-infrared light can be emitted toward the CCD camera unit from near-infrared light sources arranged opposite the CCD camera unit. Alternatively, as shown in FIGS. 11A to 11C, the light sources LSa and LSb can be arranged in upper oblique directions of a finger FG (FIG. 11A), beside the finger FG (FIG. 11B), or in lower oblique directions of the finger FG (FIG. 11C). In addition, one or plural light sources can be arranged. In short, the finger FG can be irradiated with near-infrared light from one or more light sources arranged in various directions. In this case, the external construction of the apparatus can be changed according to the arrangement positions and number of the light sources.

However, as shown in FIG. 4, by arranging two near-infrared light sources LSa and LSb on the same plane as the arrangement position of the CCD 11E to irradiate the finger FG with near-infrared light from these near-infrared light sources LSa and LSb, light sources arranged opposite the CCD 11E are unnecessary, thus simplifying the construction of the apparatus. In addition, blood vessels can be imaged only by putting a finger FG on the apparatus.

Furthermore, the above embodiments have described a case where the CCD 11E is used as a solid imaging element for performing the photoelectric conversion on the pattern light of unique tissues obtained through a body. This invention, however, is not limited to this and other kinds of solid imaging elements can be used, such as Complementary Metal Oxide Semiconductor (CMOS).

Furthermore, the above embodiments have described a case where a sensitivity adjustment means for adjusting the imaging sensitivity of the solid imaging element to unique tissues by limiting the amount of a signal which is stored per unit time through the photoelectric conversion in the solid imaging element performs reset at prescribed reset timing in the charge storage period t1 (FIG. 5A). This invention, however, is not limited to this and the reset timing in the charge storage period t1 (FIG. 5A) can be changed according to a degree of the light amount adjustment in the MCU 12. Alternatively, the reset timing in the charge storage period t1 (FIG. 5A) can be changed according to the control of the outputs of the near-infrared light sources LS. Or these methods can be combined. By doing so, the imaging sensitivity of the CCD 11E to the blood vessel pattern light can be adjusted adaptively, thus making it possible to create a blood vessel image signal S2 in which the blood vessel tissues inside a finger FG are faithfully reflected.

Furthermore, the above embodiments have described a case where visible light or near-infrared light is guided to the CCD 11E via the ultraviolet cut filter 11D arranged at a prescribed distance from the imaging surface of the CCD 11E. This invention, however, is not limited to this and an incident light selection means for selectively entering pattern light obtained through a finger into the CCD 11E can be provided.

For example, as shown in FIGS. 12A and 12B, instead of the lens 11B (FIG. 2) and the ultraviolet cut filter 11D (FIG. 2), a slide plate 80 having an RGB permeable lens 80A for letting only light of wavelengths corresponding to RGB get through because of the material of the lens and a near-infrared light permeable lens 80B for letting only light of the wavelength of a near-infrared light band because of the material of the lens is provided as the incident light selection means.

Figure 13A:
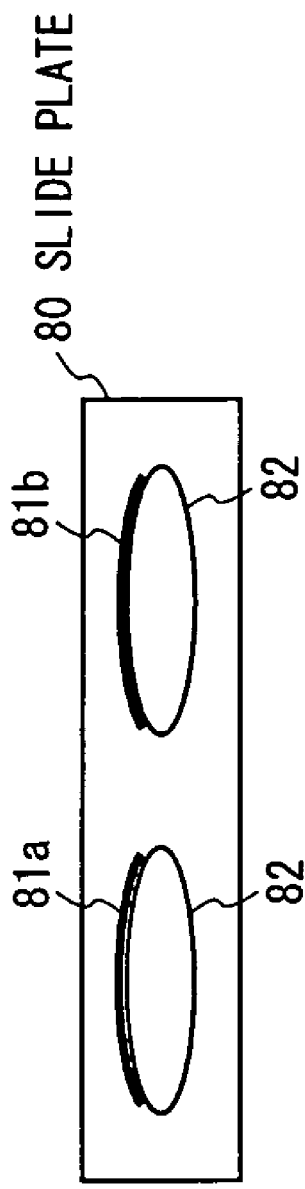
Figure 13B:
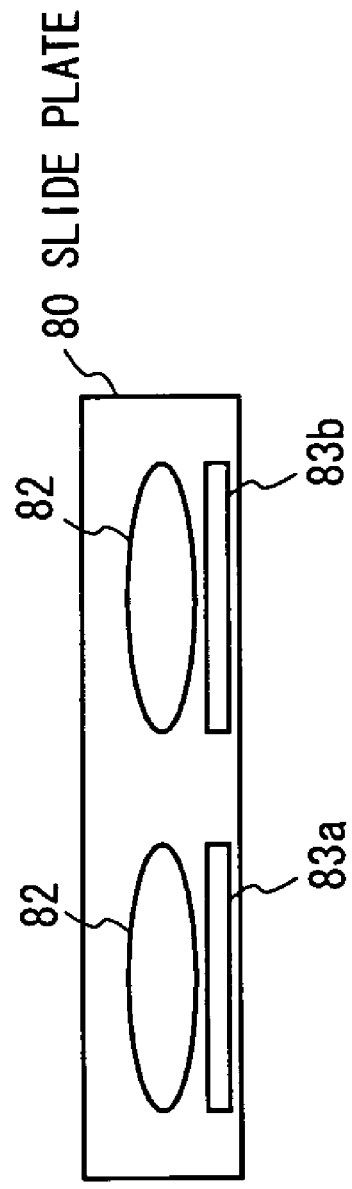
Figure 15A:
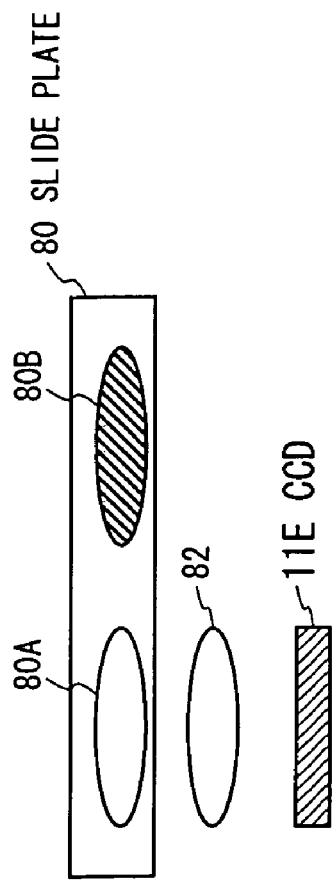
FIGS. 15A and 15B are schematic diagrams explaining insertion of lens.
Figure 15B:
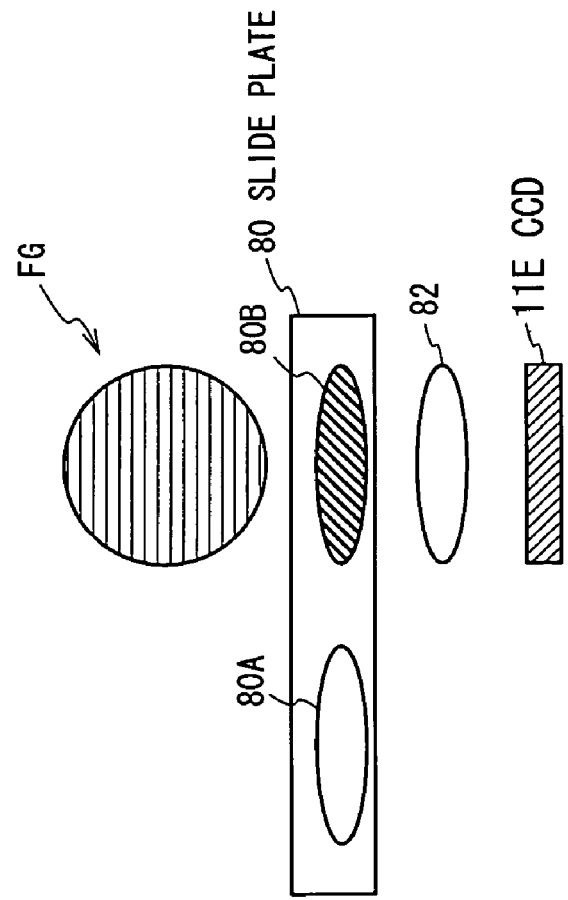

Note that, as shown in FIG. 13A, the RGB permeable lens 80A and the near-infrared light permeable lens 80B can be constructed such that thin-film coating 81a for letting only light of wavelengths corresponding to RGB get through and thin-film coating 81b for letting only light of the wavelength of the near-infrared light band get through are deposited to a normal lens 82. Alternatively, as shown in FIG. 13B, physical optical filters 83a and 83b can be used instead of the thin-film coating 81a and 81b. In addition, as the RGB permeable lens 80A, as shown in FIGS. 14A to 14C where the same reference numerals are applied to the parts corresponding to those of FIGS. 12A, 12B, 13A and 13B, only the optical filter 83b can be used. In addition, as shown in FIGS. 15A and 15B, a normal lens 82 can be provided between the slide plate 80 having the above construction and the CCD 11E.

Then the mode switching unit 20 (control unit 70) switches the slide plate 80 having such construction so as to arrange the RGB permeable filter 80A (81a, lens 82, 82 and 83a, 83a) on the CCD 11E in the normal imaging mode or arrange the near-infrared light permeable filter 80B (81b and lens 82, 82 and 83b, 83b) on the CCD 11E in the blood vessel imaging mode.

By selectively entering pattern light obtained through a finger in the blood vessel imaging mode, into the CCD 11E in this way, a blood vessel image signal S2 in which the blood vessel tissues in a finger FG is more faithfully reflected can be created. In addition, since irradiation of near-infrared light stronger than the outside light from the near-infrared light sources LS is unnecessary, the output control process for the near-infrared light sources LS and the charge adjustment process (electronic shutter) for the CCD 11E can be omitted, resulting in reducing processing loads in the imaging apparatus 10 and the portable telephone 50.

Figure 16A:
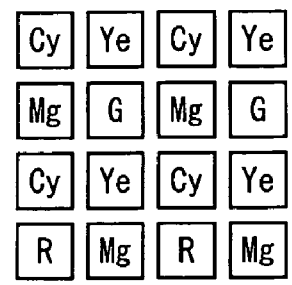
FIGS. 16A and 16B are schematic diagrams showing the construction and characteristics of a complementary color filter.
Figure 16B:
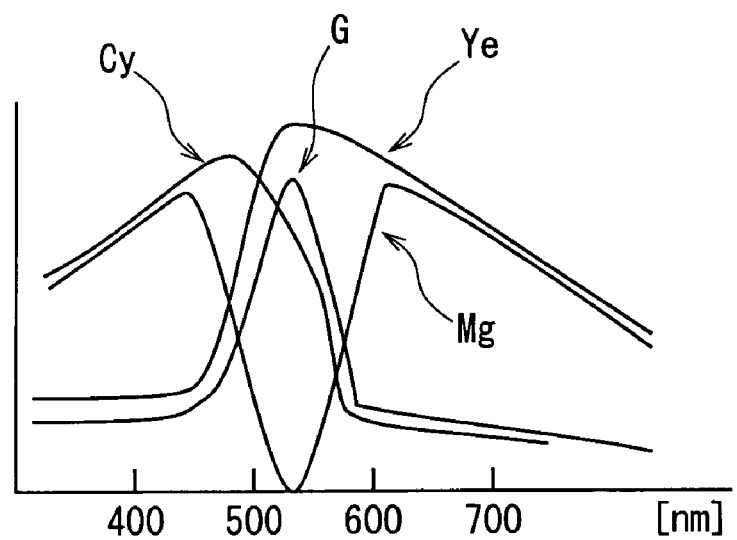

In this case, instead of the ultraviolet cut filter 11D and the above-described RGB permeable filter 80A, for example, a complementary color filter having a pixel arrangement shown in FIG. 16A and characteristics shown in FIG. 16B can be provided.

In this case, since the complementary color filter generally lets ultraviolet light get through its "Mg" region, the near-infrared light permeable filter 80B is designed to let near-infrared light get through only its pixel regions (FIG. 16A) other than the "Mg" pixel region. In addition, the signal of an imaging result is not independent by pixels in a case of normal CCDs adopting the complementary checker color difference line sequential method. Therefore in such a case, when a luminance signal is taken to Y, color difference signals are taken to Cb and Cr, with the following equations (1):

$$2n - 1th \text{ line luminance signal}: Y2n - 1 \quad (1)$$
$$= \ldots, (Cy + Mg) + (Ye + G), (Cy + Mg) + (Ye + G), \ldots$$
$$= Y(\approx 2R + 3G + 2B)$$

$$2n + 1th \text{ line luminance signal}: Y2n + 1$$
$$= \ldots, (Cy + G) + (Ye + Mg), (Cy + G) + (Ye + Mg), \ldots$$
$$= Y(\approx 2R + 3G + 2B)$$

$$2n - 1th \text{ line luminance signal}: Y2n - 1$$
$$= \ldots, (Cy + Mg) - (Ye + G), (Cy + Mg) - (Ye + G), \ldots$$
$$= Cb(\approx 2B - G)$$

$$2n + 1th \text{ line luminance signal}: Y2n + 1$$
$$= \ldots, (Cy + G) - (Ye + Mg), (Cy + G) - (Ye + Mg), \ldots$$
$$= -Cr(\approx -2R + G)$$

an addition/subtraction process is executed. By doing so, even not only a case of statically imaging blood vessels but also a case of dynamically imaging blood vessels, a blood vessel image signal S2 in which the blood vessel tissues inside a finger FG is more faithfully reflected can be created.

Furthermore, the above embodiments have described a case of putting a finger on the CCD camera unit 11 in the blood vessel imaging mode. This invention, however, is not limited to this and the finger may be fixed.

Figure 17:
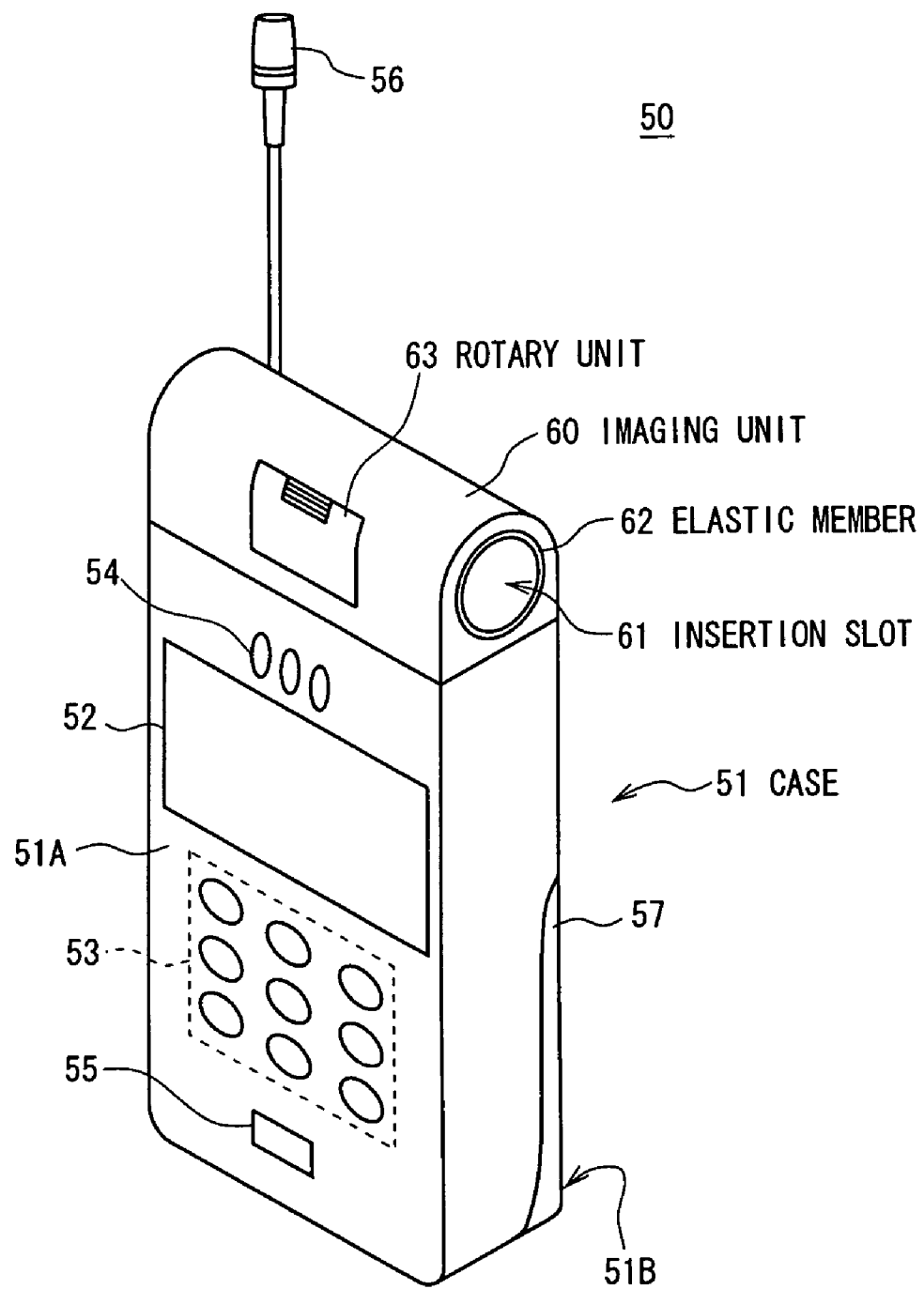
FIG. 17 is a schematic diagrams showing the external construction of a portable telephone according to another embodiment.

In this case, as shown in FIG. 17 where the same reference numerals are applied to parts corresponding to those of FIG. 7, an imaging unit for fixing a finger is provided on the case 51 as part of the portable telephone 50. Then an insertion slot 61 with a round section is formed in parallel from the right side to a position close to the left side in the imaging unit 60, and the diameter of its cross section is selected to be larger than the cross section of a forefinger of an adult. In addition, as shown in FIG. 18, a CCD camera unit 11 is provided on the front side of the inner circumference surface of the insertion slot 61 and a near-infrared light source LS is provided at the center on the back side opposite the CCD camera unit 11.

Figure 18:
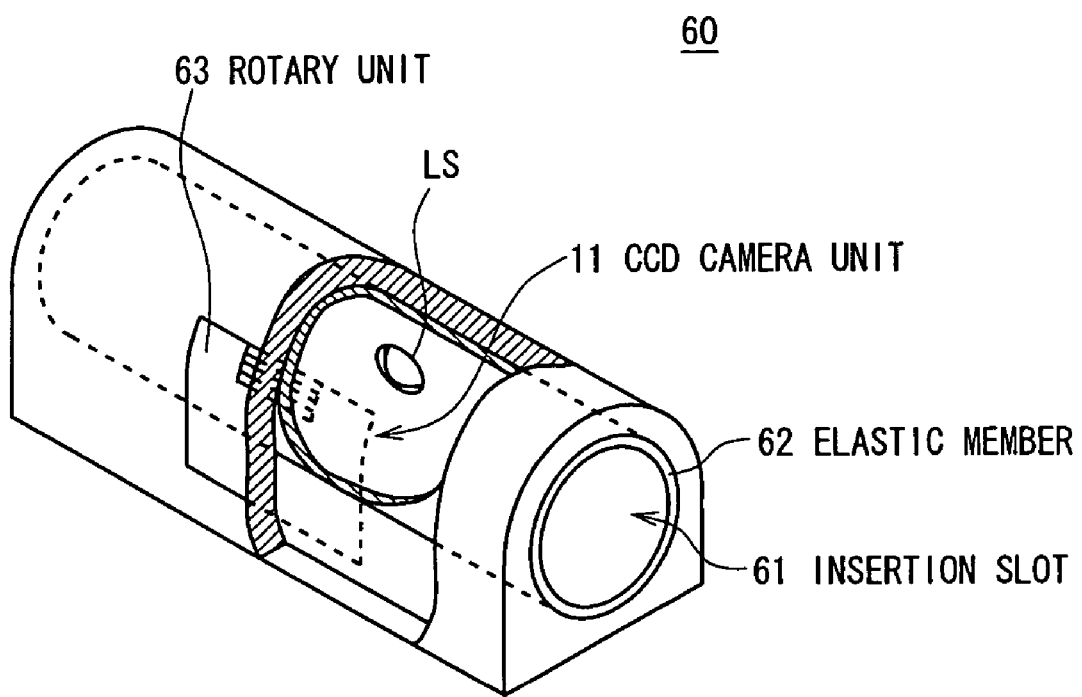
FIG. 18 is a schematic diagram showing the construction of an imaging unit.

Further, as shown in FIG. 17 and FIG. 18, elastic member of prescribed thickness such as sponge is stuck on the inner circumference surface of the insertion slot 61 excluding the CCD camera unit 11 and the near-infrared light source LS. Thereby, in this imaging unit 60, the forefinger of a cross section different from that of the insertion slot 61 can be fixed, with the result that blurring at the blood vessel imaging can be prevented.

In addition, a rotary unit 63 is provided at the front center of the imaging unit 60 so that the CCD camera unit 11 can be exposed via the rotary unit 63 outside from the inner circumference surface (FIGS. 15A and 15B) of the insertion slot 61. By doing so, the imaging unit 60 can image not only blood vessels but also normal subjects.

Furthermore, the above embodiments have described a case where the mode switching unit 20 (FIG. 2) or the control unit 70 (FIG. 9) are applied as a mode switching means for operating the irradiation means and the sensitivity adjustment means in the mode to image pattern light out of the mode to image light in the air coming from a subject and the pattern light imaging mode. This invention, however, is not limited to this and only the pattern light imaging mode can be executed.

Furthermore, the above embodiments have described a case where the portable telephone 50 is applied to install the blood vessel imaging function therein. This invention, however, is not limited to this and other various communication terminal devices having a communication function can be applied, such as information processing terminal devices including PDAs and personal computers and household electric devices.

In this case, such a communication function can be previously installed in a device, or can be externally attached to the device when necessary. In addition, other various kinds of functions can be applied, for example, for optical communication, electromagnetic wave communication or electric wave communication.

This invention can be used for a case of protecting confidence of various data from third parties and of preventing the third parties' incursion.

While there has been described in connection with the preferred embodiments of the invention, it will be obvious to those skilled in the art that various changes and modifications may be aimed, therefore, to cover in the appended claims all such changes and modifications as fall within the true spirit and scope of the invention.

What is claimed is:

1. An imaging apparatus, comprising:
   irradiation means for irradiating a body with irradiation light;
   a light detecting unit configured to detect an intensity of ambient light coming to the body;
   a light source control unit configured to control the irradiation means to irradiate the body with the irradiation light, having an intensity stronger than the ambient light coming to the body, based on the detected intensity of the ambient light coming to the body;
   a solid imaging element for performing photoelectric conversion on pattern light of unique tissues obtained through the body; and
   sensitivity adjustment means for adjusting an imaging sensitivity of said solid imaging element to the unique tissues by limiting an amount of a signal stored per unit time through the photoelectric conversion in said solid imaging element.

2. The imaging apparatus according to claim 1, wherein said irradiation means irradiates the body with light of a wavelength which has a specificity for blood vessel tissues inside the body as the irradiation light.

3. The imaging apparatus according to claim 1, wherein said irradiation means irradiates the body with light including light of a wavelength which has a specificity for blood vessel tissues of both arterial blood and venous blood inside the body as the irradiation light.

4. The imaging apparatus according to claim 1, wherein said irradiation means is provided almost on a same plane as said solid imaging element to irradiate the body on said solid imaging element with the irradiation light.

5. The imaging apparatus according to claim 1, comprising:
   mode switching means for operating said irradiation means and said sensitivity adjustment means in one of a mode to image the pattern light and a mode to image ambient light coming from a subject.

6. The imaging apparatus according to claim 5, comprising:
   incident light selection means for selectively entering the pattern light into said solid imaging element, wherein
   said mode switching means selects the pattern light by controlling said light selection means in the mode to image the pattern light.

7. The imaging apparatus according to claim 6, wherein said incident light selection means is composed of a complementary color filter having a prescribed pixel arrangement, and a filter for letting the pattern light get through only regions corresponding to some pixels of the complementary color filter.

8. The imaging apparatus according to claim 1, wherein the solid imaging element captures an image of the unique tissues of the body.

9. An imaging method, comprising:
   detecting an intensity of ambient light coming to the body;
   irradiating a body with irradiation light, having an intensity stronger than ambient light coming to the body, based on the detected intensity of the ambient light coming to the body;
   performing photoelectric conversion on pattern light of unique tissues obtained through the body, with solid imaging element; and
   adjusting an imaging sensitivity of said solid imaging element to the unique tissues by limiting an amount of a signal stored per unit time as a result of the photoelectric conversion in said solid imaging element.

10. The imaging method according to claim 9, wherein, in the irradiating step, the body is irradiated with light of a wavelength which has a specificity for blood vessel tissues inside the body as the irradiation light.

11. The imaging method according to claim 9, wherein, in the irradiating step, the body is irradiated with light including light of a wavelength which has a specificity for blood vessel tissues of both arterial blood and venous blood inside the body as the irradiation light.

12. The imaging method according to claim 9, wherein, in the irradiating step, an opposite side of the light entering in said solid imaging element is irradiated with the irradiation light.

13. The imaging method according to claim 9, wherein the irradiating step includes a mode switching step of switching to a mode to image the pattern light from a mode to image ambient light coming from a subject, wherein,
   when switching to the mode to image the pattern light is performed in the mode switching step, the body is irradiated with the irradiation light having the intensity stronger than the ambient light coming to the body.

14. The imaging method according to claim 13, wherein, in the mode switching step, an incident light selection means is controlled so as to selectively enter the pattern light into said solid imaging element in the mode to image the pattern light.

15. The imaging method according to claim 9, wherein, in the step of performing photoelectric conversion, the solid imaging element captures an image of the unique tissues of the body.

16. The communication terminal device according to claim 9, wherein the solid imaging element captures an image of the unique tissues of the body.

17. A communication terminal device having a communication function, comprising:
   irradiation means for irradiating a body with irradiation light;

a light detecting unit configured to detect an intensity of ambient light coming to the body;

a light source control unit configured to control the irradiation means to irradiate the body with the irradiation light, having an intensity stronger than the ambient light coming to the body, based on the detected intensity of the ambient light coming to the body;

a solid imaging element for performing photoelectric conversion on pattern light of unique tissues obtained through the body;

sensitivity adjustment means for adjusting an imaging sensitivity of said solid imaging element to the unique tissues by limiting an amount of a signal stored per unit time through the photoelectric conversion in said solid imaging element; and information registration means for registering a pattern signal, obtained as an imaging result of said solid imaging element, as a determination index for determining whether transmission of information is allowed.

18. The communication terminal device according to claim 17, wherein said information registration means compares a pattern of a pattern signal obtained as a result of imaging of said solid imaging element with a pattern of the registered pattern signal, to determine according to a comparison result whether the transmission of the information is allowed.

19. The communication terminal device according to claim 17, wherein said irradiation means irradiates the body with light of a wavelength which has a specificity for blood vessel tissues inside the body as the irradiation light.

20. The communication terminal device according to claim 17, wherein said irradiation means irradiates the body with light including light of a wavelength which has a specificity for blood vessel tissues of both arterial blood and venous blood inside the body as the irradiation light.

21. The communication terminal device according to claim 17, wherein said irradiation means is provided almost on a same plane as said solid imaging element and irradiates the body on said solid imaging element with the irradiation light.

22. The communication terminal device according to claim 17, comprising:

mode switching means for operating said irradiation means and said sensitivity adjustment means in one of a mode to image the pattern light and a mode to image ambient light coming from a subject.

23. The communication terminal device according to claim 22, comprising:

incident light selection means for selectively entering the pattern light into said solid imaging element, wherein said mode switching means selects the pattern light by controlling said light selection means in the mode to image the pattern light.

24. The communication terminal device according to claim 23, wherein said incident light selection means comprises a complementary color filter having a prescribed pixel arrangement, and a filter for letting the pattern light get through only regions corresponding to some pixels of the complementary color filter.

25. An imaging apparatus, comprising:

an irradiation unit configured to irradiate a body with irradiation light;

a light detecting unit configured to detect an intensity of ambient light coming to the body;

a light source control unit configured to control the irradiation unit to irradiate the body with the irradiation light, having an intensity stronger than the ambient light coming to the body, based on the detected intensity of the ambient light coming to the body;

a solid imaging element configured to perform photoelectric conversion on pattern light of unique tissues obtained through the body; and a sensitivity adjustment unit configured to adjust an imaging sensitivity of said solid imaging element to the unique tissues by limiting an amount of a signal stored per unit time through the photoelectric conversion in said solid imaging element.

26. A communication terminal device having a communication function, comprising:

an irradiation unit configured to irradiate a body with irradiation light;

a light detecting unit configured to detect an intensity of ambient light coming to the body;

a light source control unit configured to control the irradiation unit to irradiate the body with the irradiation light, having an intensity stronger than the ambient light coming to the body, based on the detected intensity of the ambient light coming to the body;

a solid imaging element configured to perform photoelectric conversion on pattern light of unique tissues obtained through the body;

a sensitivity adjustment unit configured to adjust an imaging sensitivity of said solid imaging element to the unique tissues by limiting an amount of a signal stored per unit time through the photoelectric conversion in said solid imaging element; and an information registration unit configured to register a pattern signal, obtained as an imaging result of said solid imaging element, as a determination index for determining whether transmission of information is allowed.

* * * * *